United States Patent [19]

Setier et al.

[11] Patent Number: 4,738,544
[45] Date of Patent: Apr. 19, 1988

[54] LOW TEMPERATURE AND HIGH PRESSURE FLUID FLOW CALORIMETER

[75] Inventors: Jean-Claude Setier, Pau; Gérard Alexandre, Saint Engrace; René Ladesbie, Orthez, all of France

[73] Assignee: Societe Nationale Elf Aquitaine (Production), Courbevoie, France

[21] Appl. No.: 803,163

[22] Filed: Dec. 2, 1985

[30] Foreign Application Priority Data

Nov. 30, 1984 [FR] France .................. 84 18316

[51] Int. Cl.$^4$ ............................................ G01K 17/00
[52] U.S. Cl. .......................................... 374/33; 374/31
[58] Field of Search ....................... 374/31, 32, 33, 35, 374/40, 41, 138, 135, 148, 39, 54; 422/51

[56] References Cited

U.S. PATENT DOCUMENTS

| | | | |
|---|---|---|---|
| 3,007,988 | 11/1961 | Jaffe et al. | 374/135 |
| 3,095,739 | 7/1963 | Doolittle | 374/31 |
| 3,138,436 | 6/1964 | Harmon | 422/51 |
| 3,453,880 | 7/1969 | Dropkin et al. | 374/135 |
| 3,464,267 | 9/1969 | Ehrlich et al. | 374/32 |
| 3,479,872 | 11/1969 | Tauson | 374/31 |
| 3,578,405 | 5/1971 | Woodle | 374/131 |
| 3,631,717 | 1/1972 | Kato et al. | 374/40 |
| 3,740,194 | 6/1973 | Hendy | 374/31 |
| 3,812,713 | 5/1974 | Karlsson | 374/41 |
| 4,358,208 | 11/1982 | Bahner et al. | 374/41 |
| 4,561,785 | 12/1985 | Long et al. | 374/33 |

FOREIGN PATENT DOCUMENTS 0257801 11/1969 U.S.S.R. .................. 374/35
0808924 2/1981 U.S.S.R. .................. 374/31

OTHER PUBLICATIONS

NASA Tech Brief-67-10615, "Improved Calorimeter Provides Accurate Thermal Measurements of Space Batteries", Dec. 1967.
Cryogenics, vol. 24, No. 7, Jul. 1984, pp. 339-346, Butterworth & Co., Publishers, Ltd., Guildford, Surrey, GB; H. Pieper, et al., "Measurements of Caloric Properties of Fluids at Low Temperatures and High Pressures".

Primary Examiner—Allan N. Shoap
Assistant Examiner—Thomas B. Will
Attorney, Agent, or Firm—Oblon, Fisher, Spivak, McClelland & Maier

[57] ABSTRACT

Flow calorimeter for fluids at low temperature and at high pressure essentially and which includes an electrical energy supply and two temperature sensors disposed within the fluid. The electrical energy supply includes a very tightly wound coil occupying an entire passage section of the pipe. The temperature measurements may be carried out by platinum sensors that are positioned at a predetermined distance in the pipe from the electric energy supply. Each temperature sensor can be dismantled and replaced separately.

2 Claims, 1 Drawing Sheet

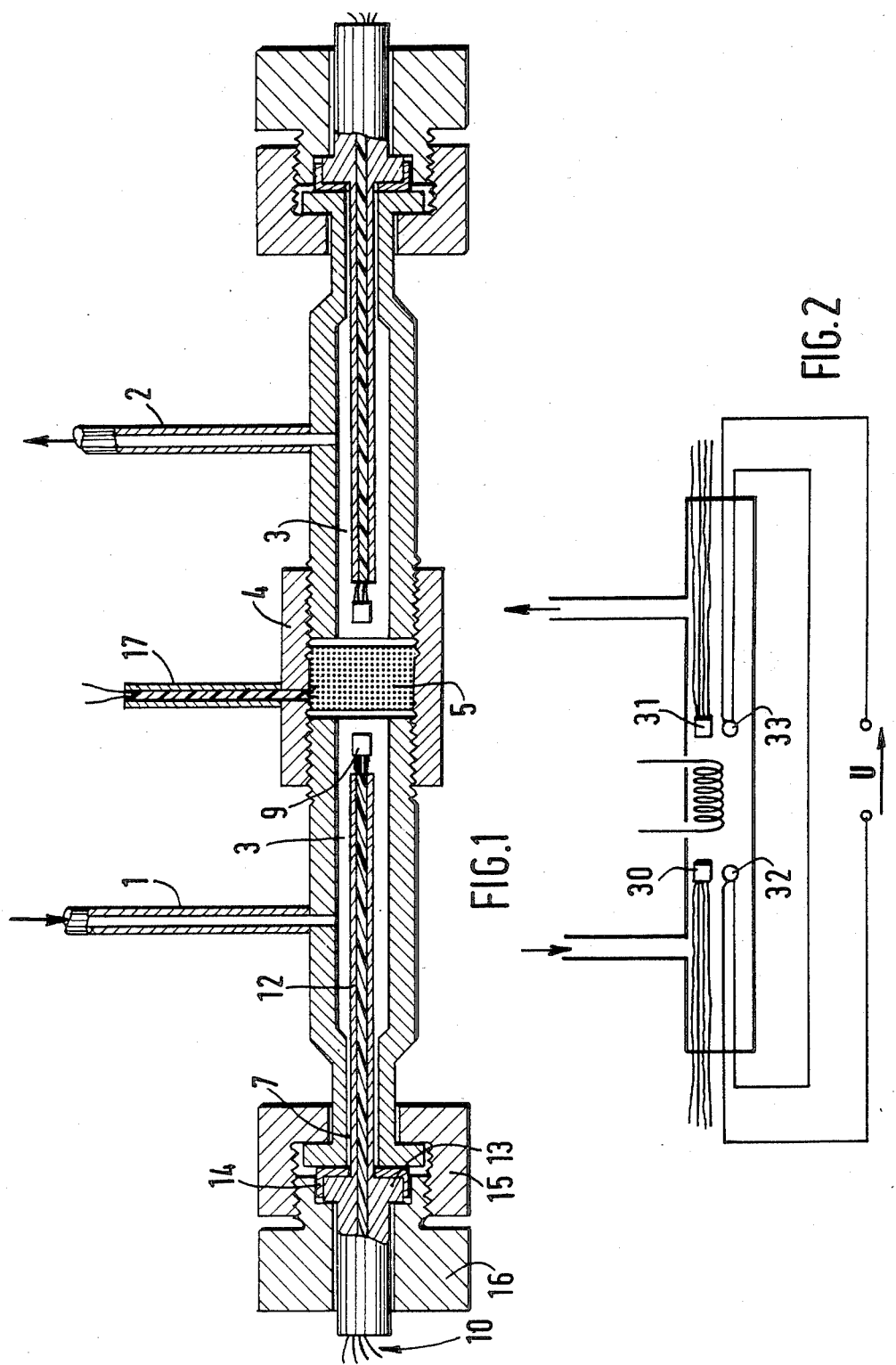

LOW TEMPERATURE AND HIGH PRESSURE FLUID FLOW CALORIMETER

BACKGROUND OF THE INVENTION

1. Field of the Invention

The invention concerns a fluid flow calorimeter and more particularly, but not exclusively, a flow calorimeter intended to measure the enthalpic differences of fluids at low temperature and at high pressure.

2. Description of the Prior Art

It is known that the constant fluid flow-rate method can produce very good results while offering a practical utilization. This method consists in causing to pass the fluid, at a predetermined temperature, with a fixed mass-flow-rate and maintaining a constant pressure, in a calorimeter where the electric power is transmitted thereto and where the temperature rise undergone by the moving fluid is measured.

The enthalpy variation corresponding to this temperature rise is equal to the electric power/fluid flow-rate ratio.

Several attempts have been made to reduce to practice this measuring principle, at low temperature and at high pressure, and among the various apparatus proposed can be cited a number of calorimeters in which the temperatures measured are the skin temperatures of the walls of the apparatus in order to prevent all possible leaks. T. MIYASAKI in "J. Chemical Thermodinamics 1980" (A New High Pressure Recycle Flow Calorimeter) proposes bringing the wires of heating resistance and the wires for simultaneously measuring the temperatures through the intermediary of a sheath, up to ambient temperature.

These devices present major drawbacks. On the one hand, they are often very space-consuming and require high flow-rates. Furthermore, they do not offer very accurate results, either because the temperatures measured are not the temperatures of the fluid itself (skin-temperature) or because the conduction due to the input sheath of the wires does not permit a real measurement of the temperature. Similarly, in certain cases, the proximity of the measuring wires and the power wires provokes an increase in temperature of the measuring wires that impairs the accuracy of the measurement.

SUMMARY OF THE INVENTION

The aim of the present invention is to overcome these drawbacks. In order to do this, the invention proposes a fluid flow-rate calorimeter having a constant fluid mass-flow-rate, at low temperature and at high pressure, fitted with an electrical power supply and at least two temperature sensors, upstream and downstream from the energy supply, characterized in that the sensors and the supply are disposed within the fluid and the corresponding electrical wires are outside the fluid independently and at the same place as the measurement.

According to the invention, the electrical current is supplied to the fluid through the intermediary of a coil wound inside the calorimeter that occupies the entire space therewithin.

Another feature of the invention is that the temperature measurements are taken by platinum sensors, the position of which it is possible to adjust in the parts immediately upstream and immediately downstream of the electric energy supply.

Another feature of the invention is that the wire outputs are rendered temperature-proof and pressure-proof through gluing. Furthermore, the calorimeter, according to the invention has small dimensions and can be completely dismantled.

The advantages obtained due to this invention are considerable. It is possible to prevent all conduction and heat leak problems by separating the power functions from the measuring functions and by ensuring that the wire outputs (independent from one another) are adjacent to the working site.

The losses through irradiation of the energy supply are minimized by it being possible to adjust the position of the temperature sensors with respect to the supply. Further, the heat exchangers between the power supply and the fluid are optimal since there is a direct contact and the resistance itself acts as exchanger.

Moreover, this calorimeter is extremely practical since it can be dismantled and allows to obtain relatively low flow-rates due to its dimensions, and is thereby product saving.

The device is also characterized in that it is possible to add to the same place as the place of the platinum sensors, thermocouples for the obtention and the verification of a perfect heat stability.

BRIEF DESCRIPTION OF THE DRAWINGS

One particular embodiment is set out herein-below in detail and with reference to the appended drawings. This embodiment is given by way of non-limitative illustration and in no way limits the scope and the spirit of the invention:

FIG. 1 represents a longitudinal cross-section of a calorimeter according to the invention;

FIG. 2 is a schematic view of a particular representation of FIG. 1.

DESCRIPTION OF THE PREFERRED EMBODIMENTS

FIG. 1 represents a longitudinal cross-section view of an example of a calorimeter according to the invention. It essentially comprises an input pipe 1 and an output pipe 2 for the fluid, that issue into the uniaxial measuring "chamber" 3. This measuring "chamber" is divided into two symmetrical portions, joined together by nut 4 in which a resistance coil 5 is wound. At each end of the "chamber" is provided an outlet 7 for the wires of the platinum sensor.

According to the present invention, once the fluid has been brought to temperature by a cryostat (not represented in FIG. 1) it is led through input pipe 1 to the measuring "chamber" 3. The measurement upstream is carried out by platinum sensor 9. This measurement is transmitted through the intermediary of the wires 10 directly towards the outside in order to be registered. These wires pass into a tube 12 that has a thicker annular portion 13 that abuts with the soft metal joint 14 upon the end of the measuring "chamber". The tube is maintained in position through screwing of the nut 15 upon the hollow bolt 16.

It is thus possible to produce a first pressure-sealing. It is necessary to provide a second sealing or tightness inside the tube for the passage of the wires. It is obtained through induction of a special glue upon a certain length of the tube and the wires. This glue, that can also act to insulate the wires must be able to maintain its properties at low temperatures and at high pressures. It is, for example, possible to utilize a glue commercialized under the trademark "ECCOBOND 285 ®" with a "Catalyst 24 LV" hardening agent.

The temperature measurement is not carried out immediately at the intersection of the pipe and the measuring "chamber" since as this is a expansion zone it is therefore unsuitable for accurate results, but it can be made between the said intersection and one end of the resistance.

The fluid thereafter passes through the small interstices of the coil 5 which occupies the entire open cross-section. The length of winding depends upon the desired power. The supply wires issue directly through the opening 17 provided in the nut 4, the tightness here also being obtained through utilization of the same type of glue as that cited herein-above.

The fluid is thus heated through the winding where the exchanges are quasi-perfect, taking into account the exchange surface at the fluid passage upon the wire. The temperature of the fluid after heating is thus measured downstream by a device identical to that described hereinabove.

FIG. 2 represents a schematic view of the calorimeter according to the invention with two platinum sensors 30 and 31 and two thermocouples 32 and 33 mounted opposite facing. It is in fact, possible to dispose at the level of each platinum sensor a thermocouple, the wires of which pass through the same tube 12 (FIG. 1).

The recording of the electromotive force U supplied by these two thermocouples allows to control the stability of the system. But, the invention is in no way limited to the embodiments described hereinabove, and on the contrary, encompasses all possible variants.

What is claimed as new and desired to be secured by Letters Patent of the United States is:

1. A flow calorimeter with constant fluid mass-flow-rate pertaining to a mass at low temperature and high pressure, comprising:
   a pipe through which said fluid passes;
   an electrical energy supply mounted within said pipe;
   an inlet and outlet pipe connected to said pipe;
   a first temperature sensor located in said pipe upstream of said electric energy supply and a second temperature sensor located in said pipe downstream of said electric energy supply wherein said energy supply comprises a tightly wound coil with small interstices formed therein, occupying an entire open cross-section of said pipe and dividing said pipe into a chamber upstream of said coil and downstream of said coil; and
   means for connecting said temperature sensors with a measuring appliance located outside said pipe, for and providing a fluid tight seal for withstanding low temperature and high pressure.

2. A calorimeter according to claim 1, wherein said means for connecting said temperature sensors with said measuring appliance comprises a rectilinear tube positioned in said pipe and a plurality of connecting wires; and adhesive means for sealing said wires in said tube and which maintains its adhesive properties at low temperatures and at high pressures, said rectilinear tube further comprising an annular portion, a metal joint and hollow bolt means for connecting said annular portion with said metal joint at at least one end portion of said pipe.

* * * * *